US012691007B2

(12) United States Patent
Govari

(10) Patent No.: US 12,691,007 B2
(45) Date of Patent: Jul. 28, 2026

(54) USER SELECTED CONFIDENCE LEVEL FOR IDENTIFICATION OF AN IMMINENT VACUUM SURGE DURING PHACOEMULSIFICATION

(71) Applicant: JOHNSON & JOHNSON SURGICAL VISION, INC., Irvine, CA (US)

(72) Inventor: Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 773 days.

(21) Appl. No.: 18/084,703

(22) Filed: Dec. 20, 2022

(65) Prior Publication Data

US 2024/0197524 A1     Jun. 20, 2024

(51) Int. Cl.
*A61F 9/007* (2006.01)
*A61M 1/00* (2006.01)
*A61M 3/02* (2006.01)

(52) U.S. Cl.
CPC ........... *A61F 9/00736* (2013.01); *A61M 1/74* (2021.05); *A61M 1/77* (2021.05); *A61M 3/0202* (2021.05); *A61M 3/0216* (2014.02); *A61B 2217/007* (2013.01); *A61F 9/00745* (2013.01); *A61M 2205/3344* (2013.01); *A61M 2210/0612* (2013.01)

(58) Field of Classification Search
CPC .. A61M 2205/3341; A61M 2205/3344; A61M 2210/0612; A61F 9/00736–00763
See application file for complete search history.

(56) References Cited

U.S. PATENT DOCUMENTS

| | | | |
|---|---|---|---|
| 5,830,176 A | 11/1998 | Mackool | |
| 7,670,330 B2 | 3/2010 | Claus et al. | |
| 8,608,681 B2 | 12/2013 | Injev | |
| 8,617,106 B2 | 12/2013 | Zacharias | |
| 9,782,064 B1 * | 10/2017 | Linder ................... | A61B 3/152 |
| 10,441,460 B2 | 10/2019 | Ross et al. | |
| 2003/0078486 A1 * | 4/2003 | Klein ..................... | A61B 3/165 |
| | | | 600/398 |

(Continued)

FOREIGN PATENT DOCUMENTS

WO       WO-2020103383 A1 *   5/2020   ........... A61F 2/1613

OTHER PUBLICATIONS

U.S. Appl. No. 17/130,409, filed Dec. 22, 2020, and titled, "A module for Aspiration and Irrigation Control".

*Primary Examiner* — Nathan R Price

(57) ABSTRACT

A system includes a user interface and a processor. The user interface is configured to receive a user-selected confidence level of measurement of intraocular pressure (IOP) for detecting vacuum surge in a phacoemulsification system. The processor is configured to (i) based on the user-selected confidence level, calculate a number of IOP readings needed during phacoemulsification procedure to identify an imminent vacuum surge, (ii) during the phacoemulsification procedure, receiving sensor readings of IOP, (iii) upon reaching the calculated number of the readings, estimate whether a consistent drop in IOP occurred between the readings, and (iv) upon estimating a consistent drop in IOP, activate an anti-vacuum surge (AVS) mechanism to mitigate the imminent vacuum surge.

10 Claims, 2 Drawing Sheets

(56)                    References Cited

U.S. PATENT DOCUMENTS

| | | | | |
|---|---|---|---|---|
| 2004/0193033 A1* | 9/2004 | Badehi | .................. | A61B 3/165 |
| | | | | 600/402 |
| 2014/0114237 A1* | 4/2014 | Gordon | .............. | A61M 3/0216 |
| | | | | 604/257 |
| 2018/0103859 A1* | 4/2018 | Provenzano | ......... | A61B 5/0024 |
| 2019/0099526 A1 | 4/2019 | Hajishah et al. | | |
| 2019/0099529 A1 | 4/2019 | Mehta et al. | | |
| 2020/0376175 A1* | 12/2020 | Hartwell | ................ | A61M 1/73 |
| 2021/0181932 A1* | 6/2021 | Han | .................... | G06F 3/04847 |
| 2022/0192878 A1 | 6/2022 | Algawi et al. | | |
| 2022/0331512 A1 | 10/2022 | Baxter et al. | | |

* cited by examiner

USER SELECTED CONFIDENCE LEVEL FOR IDENTIFICATION OF AN IMMINENT VACUUM SURGE DURING PHACOEMULSIFICATION

FIELD OF THE DISCLOSURE

The present disclosure relates generally to phacoemulsification apparatuses and probes, and particularly to systems and methods for control of intraocular pressure (IOP).

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

The present disclosure will be more fully understood from the following detailed description of the examples thereof, taken together with the drawings in which:

DETAILED DESCRIPTION OF EXAMPLES

Overview

Figure 1:
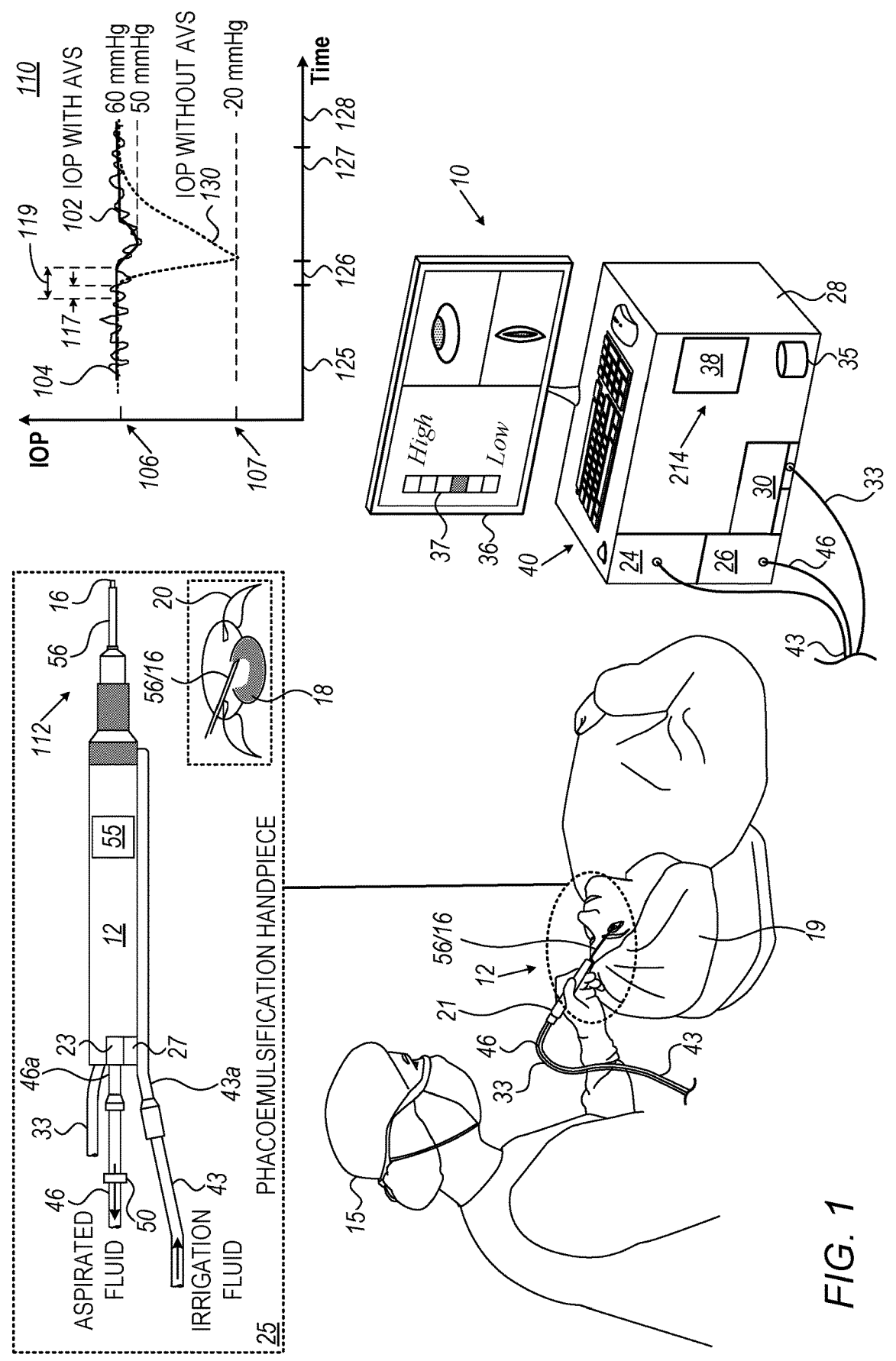
FIG. 1 is a schematic, pictorial view, along with an orthographic side view, of a phacoemulsification apparatus, in accordance with an example of the present disclosure.

During phacoemulsification of an eye lens, if an emulsified lens particle fully blocks the inlet of the aspiration tip, a high vacuum occurs in the aspiration line. After the vacuum buildup, when the line becomes unblocked (e.g., by the particle being subsequently sucked into the line), the high vacuum in the line leads to the eye experiencing a surge in aspiration suction power (also called hereinafter a "vacuum surge") with potentially traumatic consequences to the eye as the intraocular pressure (IOP) abruptly falls. For example, exposing the eye to suction power leading to a too low IOP (e.g., below 20 mmHg) may cause the eye chamber to collapse.

A recent solution to the problem of automatically detecting and mitigating vacuum surges is described in U.S. patent application Ser. No. 17/130,409, filed on Dec. 22, 2020, and titled, "A module for Aspiration and Irrigation Control,"

whose disclosure is incorporated herein by reference. The application discloses an anti-vacuum surge (AVS) mechanism (e.g., an AVS module) coupled to the phacoemulsification probe, which prevents a sudden vacuum increase being transferred to the eye when an occlusion breaks (i.e., prevents vacuum surge). For example, the module can mitigate the vacuum surge by closing off a connection from the aspiration line to the eye at the distal side of the module as soon as an occlusion break (post vacuum surge) is detected.

The onset of the occlusion break, however, is difficult to timely detect due to IOP reading fluctuations and the quick response time that is typically required to prevent damage to the surgical site. Such fluctuations can be caused by various reasons, such as varying irrigation flow or the amount of emulsified lens particles that are aspirated through the aspiration tip (e.g., a hollow needle). The small volume of the lens capsule makes such variations impact IOP. During a very short time duration scale (e.g., a few tens of milliseconds) such fluctuations resemble an onset of a vacuum surge (e.g., a decisive drop in IOP).

To totally avoid any risk of vacuum surge, a very quick response is required by activating the AVS mechanism after, for example, few tens of milliseconds of measuring an IOP drop. However, such a fast reaction to a drop in IOP may result in over-activation of the AVS module, which in turn leads to a degradation of "followability," a measure of phacoemulsification process effectiveness.

Followability is the ability to attract cataract pieces to the phacoemulsification tip. Sufficient followability is important for efficient and safe phacoemulsification. An overly cautious system (or user) regarding vacuum surges as the tip is placed or moved within the eye lens causes the system to interrupt suction (e.g., using the AVS mechanism) at any slight indication of IOP drop, and such overuse of AVS degrades followability.

As the physician must still avoid the aforementioned traumatic consequences to the eye due to vacuum surges, such a restriction to followability may cause the physician to perform the phacoemulsification process too slowly, thereby leading to practical ineffectiveness.

Examples of the present disclosure that are described hereinafter provide methods and systems to allow a physician performing phacoemulsification to select a confidence level in an imminent occurrence of a vacuum surge, so as to optimally and automatically identify and mitigate the coming surge.

The confidence level is based on the number of pressure/vacuum sensor readings needed to identify an onset of the vacuum surge by capturing a sufficiently consistent drop in IOP. A too low confidence level, which relies on a small number of readings (e.g., over a time duration that may range between several milliseconds to several tens of milliseconds, may produce too many false positives which leads to needless activation of the AVS system. Unnecessary activation of the AVS significantly reduces followability. A too high confidence level, which relies on a large number of readings (e.g., over a time duration that may range between few hundred milliseconds and several hundred milliseconds, may produce fewer false positive alerts. However, waiting for an extended duration may delay the processor from activating the AVS mechanism in sufficient time to prevent a surge.

The physician may therefore adjust the confidence level as needed, based on experience, so as to bring it to some mid-value optimum that is user dependent.

Performance of the identification may be improved over time based on data accumulated during the procedure. A system processor may look retrospectively at the procedure to determine whether or not an event was a vacuum surge. Machine learning may be used to improve performance, and such machine learning may be physician specific to take into account the particular physician's way of working and therefore propose an optimal confidence level for that physician.

Using an optimal confidence level setting point results in precise activation of the AVS mechanism, which both prevents extreme, and more rare events, of vacuum surges, as well as maintains a high clinical effectiveness (by avoiding a degraded followability).

Delayed time responses may be further reduced by using a microprocessor (e.g., a STM32 microprocessor) to control activation of the anti-vacuum surge (AVS) mechanism (e.g., an AVS module) based on the pressure readings. The microprocessor sends each command with negligible delay, e.g., ~1 microseconds.

In an example, a system is provided that comprises a graphical user interface (GUI) configured to receive user selection of a confidence level on IOP for detecting vacuum surge in a phacoemulsification system. A processor of the system is configured to calculate a minimal number of IOP readings during a phacoemulsification procedure, based on a user-selected confidence level, that is needed to identify an imminent vacuum surge. During phacoemulsification, the processor receives IOP sensor readings, and upon reaching the minimal number of readings, the processor estimates if there is a consistent drop in IOP (e.g., a monotonically dropping moving average IOP) between the received readings. If there is a consistent drop in IOP, the processor activates an anti-vacuum surge (AVS) mechanism to mitigate the imminent vacuum surge.

In another example, the processor is configured to update the confidence level during the procedure based on data accumulated during the procedure. For example, the processor uses a higher confidence level at the start of the procedure, meaning that the processor requires a certain number of measurements to reach a decision. By the middle of the procedure, the processor checks if it is able to identify the same trends it detected using fewer measurements. If so, the processor reduces the confidence level needed to identify an imminent surge.

The processor may be further configured to present a recommended confidence level on the GUI, for user selection, that is based on data during accumulated other phacoemulsification procedures performed by the same user.

As indicated above, the processor can be configured to train a machine learning (ML) algorithm to infer and recommend a confidence level for the user to select, wherein the processor is configured to train the ML algorithm using a database of changes to the selected confidence level made by that user during past phacoemulsification procedures.

Apparatus Description

FIG. 1 is a schematic, pictorial view, along with an orthographic side view, of a phacoemulsification apparatus 10, in accordance with an example of the present disclosure.

As seen in the pictorial view of phacoemulsification apparatus 10, and in the schematic side view inset 25, a phacoemulsification probe 12 (e.g., a handpiece) comprises a distal end 112 comprising a needle 16 and a coaxial irrigation sleeve 56 that at least partially surrounds needle 16 and creates a fluid pathway between the external wall of the needle and the internal wall of the irrigation sleeve, where needle 16 is hollow to provide an aspiration channel. More-over, the irrigation sleeve may have one or more side ports at or near the distal end to allow irrigation fluid to flow toward the distal end of the handpiece through the fluid pathway and out of the port (s).

Needle 16 is configured for insertion into a lens capsule 18 of an eye 20 of a patient 19 by a physician 15 to remove a cataract. While needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Irvine, CA, USA.

In the shown example, during the phacoemulsification procedure an irrigation pump 24, comprised in a console 28, pumps irrigation fluid from an irrigation reservoir (not shown) to the irrigation sleeve 56 to irrigate the eye. The fluid is pumped via an irrigation tubing line 43 running from console 28 to an irrigation channel 43a of probe 12. In another example, pump 24 may be coupled with or replaced by a gravity-fed irrigation source such as a balanced salt solution bottle/bag.

Eye fluid and waste matter (e.g., emulsified parts of the cataract) are aspirated via hollow needle 16 to a collection receptacle (not shown) by a processor-controlled aspiration pump 26, also comprised in console 28, using aspiration tubing line 46 running from aspiration channel 46a of probe 12 to console 28.

In the shown example, probe 12 includes an irrigation pressure sensor 27 coupled with irrigation channel 43a and an aspiration vacuum level sensor 23 coupled with an aspiration channel 46a. Sensor 27 may be positioned anywhere along tubing line 43 or channel 43a. Likewise, sensor 23 may be positioned anywhere along tubing line 43 or channel 43a.

Channels 43a and 46a are coupled respectively with irrigation line 43 and aspiration line 46. Pumps 24 and 26 may be any pump known in the art (e.g., peristaltic pump, progressive cavity pump). Using sensors (e.g., as indicated by sensors 27 and/or 23), a processor 38 controls a flow rate of irrigation pump 24 and/or aspiration pump 26 to maintain IOP within prespecified limits. In some cases, typically to protect against a vacuum surge hazard, the system activates AVS module 50 (seen in inset 25) to disconnect aspiration channel 46a from line 46 and aspiration pump 26. AVS module 50 can be autonomous, with a processor inside AVS 50 that receives and processes sensor readings and commands activation of module 50, or module 50 can be commanded from processor 38.

As noted above, processor 38 may control the flow rate of irrigation pump 24 and/or aspiration pump 26, where one of the software modules running in processor 38 is a proportional-integral-derivative (PID) controller 214.

Processor 38 estimates the IOP using readings from the irrigation pressure sensor 27 and an optional empirical offset, if the irrigation pressure is measured at the proximal end of handpiece 12. Readings of sensor 23 gives the vacuum level (also called sub-pressure) inside the aspiration channel.

Sensors 27 and 23 may be any sensor known in the art, including, but not limited to, a vacuum sensor or flow sensor. The sensor measurements (e.g., of pressure, vacuum, and/or flow) may optionally be taken as close to the distal end of the handpiece where the irrigation outlet and the aspiration inlet are located, so as to provide processor 38 with an accurate indication of the actual measurements occurring within an eye and provide a short response time to a control loop comprised in processor 38.

In an example, the same pressure sensor model is used to measure irrigation pressure and aspiration sub-pressure, using different sensor settings/calibrations.

As further shown, phacoemulsification probe 12 includes a piezoelectric crystal 55, coupled to a horn (not shown), that drives needle 16 to vibrate in a resonant vibration mode that is used to break a cataract into small pieces during a phacoemulsification procedure. Console 28 comprises a piezoelectric drive module 30, coupled with the piezoelectric crystal, using electrical wiring running in cable 33.

Processor 38 may receive user-based commands via a user interface 40, which may include setting a vibration mode and/or frequency of the piezoelectric crystal, and setting or adjusting an and/or aspiration rate of the irrigation pump 24 and aspiration pump 26. Optionally, user interface 40 includes a foot pedal. Processor 38 may receive user-based commands via a user interface 40, which may include needle 16 stroke amplitude settings and turning on irrigation and/or aspiration. In an example, the physician uses a foot pedal (not shown) as a means of control. For example, foot pedal position one activates only irrigation, pedal position two activates both irrigation and aspiration, and pedal position three adds needle 16 vibration. Additionally, or alternatively, processor may receive the user-based commands from controls located in a handle 21 of probe 12.

Some or all of the functions of processor 38 may be combined in a single physical component or, alternatively, implemented using multiple physical components. These physical components may comprise hard-wired or programmable devices, or a combination of the two. In some examples, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 is simplified for clarity of presentation. For example, the disclosed AVS scheme may be applied using alternative or additional control devices of the system, such as other valves (e.g., a bypass valve).

Selecting a Confidence Level for Detecting and Mitigating Vacuum Surge

Graph 110 of FIG. 1 provides an example of how the disclosed technique uses a confidence level in IOP for timely detection and mitigation of a vacuum surge. Graph 110 shows schematically a typical smoothed curve (102) of a vacuum surge. As seen, during time duration 125 the system maintains a certain IOP level 106. Then there is an occlusion. The IOP may increase in such case, however, the increase is shown retained at level 106 using, for example, control over irrigation flow. When the occlusion breaks there is a drop in IOP (vacuum surge) 130. At some point the AVS is activated to reverse the IOP dip before it reaches a hazardous level 107.

As described above, the allowable IOP working range during phacoemulsification is typically between a low IOP limit 107 (e.g., −20 mmHg) and some high IOP limit (e.g., 120 mmHg). Physician 15 typically works (e.g., during time durations 125 and 128) at a nominal TOP level 106.

Curve 102 is an idealized smooth variation in IOP that may be caused by partial or full blockage of the inlet of needle 16. As seen, when the occlusion breaks without mitigation an abrupt dip 130 in IOP (i.e., vacuum surge 130) occurs over time duration 127, and potentially harmful strong suction force is applied to the eye material.

The disclosed system is configured to apply AVS module 50 so avoid vacuum surge 130 that may damage the eye. However, curve 102 is an idealized smooth description of changes in the IOP. An actual curve 104 demonstrates how IOP fluctuations make it hard for an algorithm to decide if and when to activate AVS module 50.

To overcome fluctuations, system 10 allows physician 15 to select a confidence level in IOP. In the example of FIG. 1, user interface 40 and display 36 may be integrated into a touch screen graphical user interface (GUI). Display 36 shows a confidence level scale 37 that physician 15 can use to select a given discrete level.

The confidence level is based on the number of readings needed to identify an imminent vacuum surge. A high confidence level requires a large number of readings at the expense of slow response time. This is manifested in a longer acquisition interval 119 of sensor 27 readings. Using a high confidence level reduces the probability that one of the IOP drops towards local minima in IOP during time duration 126 will be erroneously identified as an onset of a vacuum surge. This robustness keeps 10 high followability. However, an excessively high confidence level (that translates to a too long duration 119) will cause late identification of a true vacuum surge.

A lower confidence level requires only a small number of readings, yielding a faster response time but also a certain rate of false positive alerts. This is manifested schematically in a shorter acquisition interval 117 of sensor 27 readings. If duration 117 is too short, AVS 50 will be activated during duration 126 (and even during time periods 125 and 128) before every instance when IOP drops toward local minima, which strongly suppresses followability.

For each user there exists some intermediate confidence level in IOP. In the example of FIG. 1, display 36 shows a discrete confidence level scale 37. The physician may therefore adjust the confidence level, as needed, based on experience.

In other examples, the user may adjust the confidence level with a virtual slide ruler, enter a numerical value, or make a verbal instruction.

Figure 2:
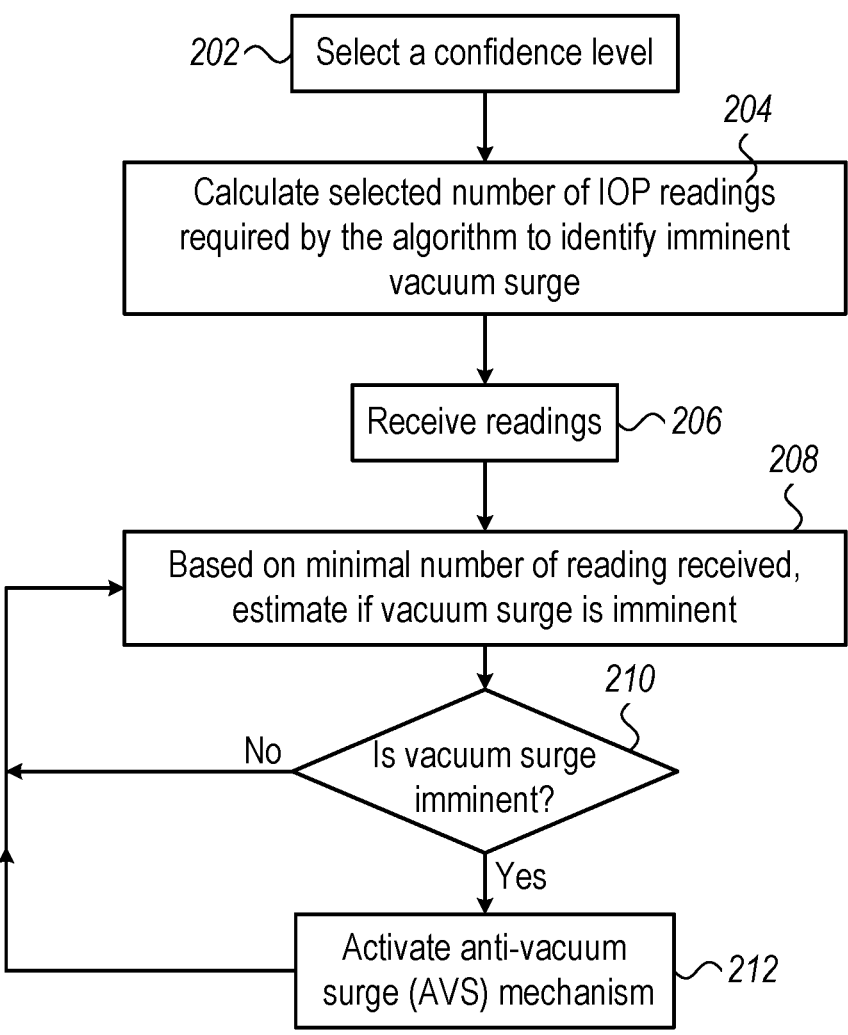
FIG. 2 is a flow chart schematically illustrating a method to identify an imminent vacuum surge during phacoemulsification and mitigate its occurrence, in accordance with an example of the present disclosure.

FIG. 2 is a flow chart schematically illustrating a method to identify an imminent vacuum surge during phacoemulsification and mitigate its occurrence (steps 202-212), in accordance with an example of the present disclosure. FIG. 2 also includes a block of adaption-based retrospective analysis on accumulated actual results (steps 214-224).

The algorithm, according to the presented example, carries out a process that begins with physician 15 selecting a confidence level or accepting a system selection, at a confidence level setting step 202.

Next, at a calculation step 204, the processor calculates a calculated (e.g., selected) number of IOP readings required by the algorithm to identify an imminent vacuum surge, for example, by identifying a consistent monotonic decline in IOP over the time duration of the readings that is associated with the confidence level. The calculation can be based on a monotonic relation between confidence level and readings number that is obtained experimentally (e.g., a linear relation with the coefficient that is determined empirically).

Next, during phacoemulsification, processor 38 receives readings, at IOP readings receiving step 206.

Based on the minimal number of readings received, the processor estimates (e.g., by checking if a moving average of the readings shows a consistent drop in IOP) if vacuum surge is imminent, at a vacuum surge occurrence estimation step 208.

If the processor concludes that a vacuum surge is imminent, (Yes at a decision step 210), the processor activates the AVS mechanism, at an AVS activation step 212.

Optionally, processor 38 checks if the confidence level requires an update, either due to too many false positive AVS activations (requiring an increase in confidence level) or too many missed vacuum surge events. The physician can adjust the confidence level during a procedure or after a procedure to a level that feels comfortable for the physician and for a particular procedure being performed.

Optionally, at the end of a procedure, processor 38 may suggested an updated confidence level based on accumulated data from one or more procedures performed by the physician. In some example embodiments, processor 38 receives input from the physician or clinical professional based on which, processor 38 may compute an adjusted confidence level. Optionally, a machine learning algorithm may be applied to adapt a suggested confidence level to the skill and style of the physician.

EXAMPLES

Example 1

A system (10) includes a user interface (40) and a processor (38). The user interface is configured to receive a user-selected confidence level (37) of measurement of intraocular pressure (IOP) for detecting vacuum surge in a phacoemulsification system. The processor is configured to (i) based on the user-selected confidence level, calculate a number of IOP readings needed during phacoemulsification procedure to identify an imminent vacuum surge, (ii) during the phacoemulsification procedure, receiving sensor (27) readings of IOP, (iii) upon reaching the calculated number of the readings, estimate whether a consistent drop in IOP occurred between the readings, and (iv) upon estimating a consistent drop in IOP, activate an anti-vacuum surge (AVS) mechanism (50) to mitigate the imminent vacuum surge.

Example 2

The system (10) according to example 1, wherein the calculated number of IOP readings grows with the user-selected confidence level (37).

Example 3

The system (10) according to any of examples 1 and 2, wherein the processor (38) is configured to adjust the user-selected confidence level (37) during the phacoemulsification procedure based on AVS (50) activation data accumulated during the phacoemulsification procedure.

Example 4

The system (10) according to any of examples 1 through 3, wherein the processor (38) is further configured to, based on accumulated data during other phacoemulsification procedures performed by a same user, present to the user a user-specific recommended confidence level (37) for the user to select.

Example 5

The system (10) according to any of examples 1 through 4, wherein the user interface (40) is configured to receive the user-selected confidence level (37) by the user adjusting a virtual slide ruler.

Example 6

The system (10) according to any of examples 1 through 4, wherein the user interface (40) is configured to receive the user-selected confidence level (37) by the user selecting a level out of a set of discrete levels.

Example 7

The system (10) according to any of examples 1 through 4, wherein the user interface (40) is configured to receive the user-selected confidence level (37) by the user entering a numerical value of the user-selected confidence level.

Example 8

The system (10) according to any of examples 1 through 4, wherein the user interface (40) is configured to receive the user-selected confidence level (37) by receiving a verbal instruction made by the user.

Example 9

The system (10) according to any of examples 1 through 8, wherein the processor (38) is configured to activate the AVS mechanism (50) by activating a valve to close an aspiration line (46) of the phacoemulsification system.

Example 10

The system (10) according to any of examples 1 through 9, wherein the processor (38) is configured to train a machine learning (ML) algorithm to infer and recommend a user-specific confidence level (37) for the user to select, wherein the processor is configured to train the ML algorithm using a plurality of recorded changes to the selected confidence level (37) that the same user made during past phacoemulsification procedures.

Example 11

A method includes receiving a user-selected confidence level (37) of measurement of intraocular pressure (IOP) for detecting vacuum surge in a phacoemulsification system (10). A number of IOP readings needed during phacoemulsification procedure to identify an imminent vacuum surge is calculated based on the user-selected confidence level. Sensor (27) readings of IOP are received during the phacoemulsification procedure. Upon reaching the calculated number of the readings, it is estimated whether a consistent drop in IOP occurred between the readings. Upon estimating a consistent drop in IOP, an anti-vacuum surge (AVS) mechanism (50) is activated to mitigate the imminent vacuum surge.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:

a user interface, configured to receive a user-selected confidence level of measurement of intraocular pressure (IOP) for detecting vacuum surge in a phacoemulsification system; and a processor, which is configured to:

based on the user-selected confidence level, calculate a number of IOP readings needed during phacoemulsification procedure to identify an imminent vacuum surge;

during the phacoemulsification procedure, receive sensor readings of IOP;

upon reaching the calculated number of the readings, estimate whether a consistent drop in IOP occurred between the readings; and upon estimating a consistent drop in IOP, activate an anti-vacuum surge (AVS) mechanism to mitigate the imminent vacuum surge.

2. The system according to claim 1, wherein the calculated number of IOP readings grows with the user-selected confidence level.

3. The system according to claim 1, wherein the processor is configured to adjust the user-selected confidence level during the phacoemulsification procedure based on AVS activation data accumulated during the phacoemulsification procedure.

4. The system according to claim 1, wherein the processor is further configured to, based on accumulated data during other phacoemulsification procedures performed by a same user, present to the user a user-specific recommended confidence level for the user to select.

5. The system according to claim 1, wherein the user interface is configured to receive the user-selected confidence level by the user adjusting a virtual slide ruler.

6. The system according to claim 1, wherein the user interface is configured to receive the user-selected confidence level by the user selecting a level out of a set of discrete levels.

7. The system according to claim 1, wherein the user interface is configured to receive the user-selected confidence level by the user entering a numerical value of the user-selected confidence level.

8. The system according to claim 1, wherein the user interface is configured to receive the user-selected confidence level by receiving a verbal instruction made by the user.

9. The system according to claim 1, wherein the processor is configured to activate the AVS mechanism by activating a valve to close an aspiration line of the phacoemulsification system.

10. The system according to claim 1, wherein the processor is configured to train a machine learning (ML) algorithm to infer and recommend a user-specific confidence level for the user to select, wherein the processor is configured to train the ML algorithm using a plurality of recorded changes to the selected confidence level that the same user made during past phacoemulsification procedures.

* * * * *